United States Patent [19]

Allen et al.

[11] Patent Number: 5,498,802
[45] Date of Patent: Mar. 12, 1996

[54] PROCESS FOR PREPARING OMEGA-HALO-KETONES

[75] Inventors: Diane E. Allen; Ramakrishnan Chidambaram, both of Corpus Christi, Tex.

[73] Assignee: Hoechst Celanese Corporation, Sommerville, N.J.

[21] Appl. No.: 395,333

[22] Filed: Feb. 28, 1995

[51] Int. Cl.$^6$ .................................................. C07C 49/16
[52] U.S. Cl. ................................... 568/495; 568/838
[58] Field of Search ............................ 568/383, 403, 568/407, 419, 495, 416, 838

[56] References Cited

U.S. PATENT DOCUMENTS

| | | | |
|---|---|---|---|
| 2,497,349 | 2/1950 | Farkas. | |
| 4,189,469 | 2/1980 | Gleixner et al. | 568/764 |
| 4,260,845 | 9/1981 | Shioyama | 585/640 |
| 4,588,846 | 5/1986 | Mitsui et al. | 568/835 |
| 4,661,639 | 4/1987 | Tojo et al. | 568/835 |
| 4,849,550 | 7/1989 | Shirafuji et al. | 568/899 |

*Primary Examiner*—Werren B. Lone
*Attorney, Agent, or Firm*—James J. Mullen; Donald R. Cassady

[57] ABSTRACT

A process for preparing 6-chloro-2-hexanone which comprises the steps of (a) dehydrating cyclohexanol in the presence of a suitable catalyst and at a suitable temperature and for a sufficient period of time to form cyclohexene; (b) rearranging said cyclohexene at a higher temperature than in step (a) in the presence of a suitable catalyst and for a sufficient period of time to form 1-methylcyclopentene; (c) hydrating said 1-methylcyclopentene at a temperature lower than step (b) and in the presence of a resin catalyst for a sufficient period of time to form 1-methylcyclopentanol; (d) reacting said 1-methylcylcopentanol with a suitable amount of an alkali metal hypochlorite in the presence of a carboxylic acid to form 1-methylcyclopentyl hypochlorite; and (e) heating said 1-methylcyclopentyl hypochlorite for a sufficient period of time to form 6-chloro-2-hexanone.

31 Claims, No Drawings

PROCESS FOR PREPARING OMEGA-HALO-KETONES

BACKGROUND OF THE INVENTION

1. Field of the Invention

The present invention is directed to a novel process for preparing omega-halo-ketones such as 6-chloro-2-hexanone.

6-Chloro-2-hexanone is a final intermediate in the manufacture of the vasodilator drug pentoxifylline, commonly sold under the trademark Trental. The current manufacturing process for 6-chloro-2-hexanone is a three-step process starting from ethyl acetoacetate such as that described in *Organic Synthesis*, Collective Volume 5, Gilman, H. Ed.; John Wiley, N.Y. (1932), pages 248–251 and 350–353. Atom efficiency of this process is modest (37%), since a molecule, each of ethanol and carbon dioxide, are lost per molecule of product made. Sodium bromide is formed as a by-product, making waste disposal an issue as well. Consequently, it is desirable to overcome these deficiencies and provide a more efficient, low-cost method to produce 6-chloro-2-hexanone.

2. Description of the Prior Art

The following prior art references are disclosed in accordance with the terms of 37 CFR 1.56, 1.93, and 1.97.

U.S. Pat. No. 2,497,349 discloses a process for preparing alicyclic alcohols from various hydrocarbons including methylcyclopentane.

U.S. Pat. No. 2,615,921 discloses a process for the oxidation of naphthenic hydrocarbons including methylcyclopentane.

U.S. Pat. No. 2,675,402 discloses a process for preparing tertiary cycloaliphatic hypohalites such as methylcyclopentyl hypochlorite.

U.S. Pat. No. 2,691,682 discloses a process for preparing omega-halo-ketones by rearrangement of tertiary cycloaliphatic hypohalites including the preparation of 6-chlorohexan-2-one by rearrangement of 1-methylcyclopentyl hypochlorite.

U.S. Pat. No. 3,391,190 discloses a continuous process for oxidizing lower alkanes and cycloalkanes, particularly cyclohexane, to ketones and alcohols.

U.S. Pat. No. 3,737,433 discloses certain oxoalkyldimethyl-xanthines for use in the pharmaceutical area.

U.S. Pat. No. 4,189,469 discloses pharmaceutical compositions for oral administration containing xanthine derivatives.

U.S. Pat. No. 4,260,845 discloses a zinc aluminate dehydration catalyst, suitably activated, as by heating in air, which is employed to dehydrate a saturated alcohol (such as cyclohexanol) to produce an olefin.

U.S. Pat. No. 4,588,846 discloses a process for producing a cyclic alcohol (such as cyclopentanol) by catalytic hydration of a cyclic olefin (such as cyclopentene) in a liquid phase.

U.S. Pat. No. 4,661,639 discloses a process for producing a cyclic alcohol (such as cyclohexanol) by catalytic hydration of a cyclic olefin (such as cyclohexene).

U.S. Pat. No. 4,849,550 discloses a method for producing cycloalkanols by the hydration of cycloalkenes (such as methylcyclopentane) with aromatic sulfonic acids as a catalyst.

*Journal of the American Chemical Society,* December 1948, pp. 4041–4045 discloses the isomerization of cyclohexenes to cyclopentenes.

All of the above cited prior art and any other references mentioned herein are incorporated herein by reference in their entirety.

SUMMARY OF THE INVENTION

The present invention provides a novel and efficient process for preparing 6-chloro-2-hexanone which comprises the steps of (a) dehydrating cyclohexanol in the presence of a suitable catalyst and at a suitable temperature and for a sufficient period of time to form cyclohexene; (b) rearranging said cyclohexene, at a higher temperature than in step (a), in the presence of a suitable catalyst and for a sufficient period of time to form 1-methylcyclopentene; (c) hydrating said 1-methylcyclopentene, at a temperature lower than step (b) and in the presence of a resin catalyst for a sufficient period of time to form 1-methylcyclopentanol; (d) reacting said 1-methylcyclopentanol with a suitable amount of an alkali metal hypochlorite in the presence of a carboxylic acid to form 1-methylcyclopentyl hypochlorite; and (e) heating said 1-methylcyclopentyl hypochlorite for a sufficient period of time to form 6-chloro-2-hexanone.

DETAILED DESCRIPTION OF THE INVENTION

The present invention provides a very efficient process for preparing 6-chloro-2-hexanone (sometimes referred to as CHO) utilizing readily available and commercial starting materials and provides a process which does not produce unwanted by-products. Generally, this process for preparing 6-chloro-2-hexanone comprises the steps of (a) dehydrating cyclohexanol in the presence of a suitable catalyst and at a suitable temperature and for a sufficient period of time to form cyclohexene; (b) rearranging said cyclohexene at a higher temperature than in step (a) in the presence of a suitable catalyst and for a sufficient period of time to form 1-methylcyclopentene; (c) hydrating said 1-methylcyclopentene at a temperature lower than step (b) and in the presence of a resin catalyst for a sufficient period of time to form 1-methylcyclopentanol; (d) reacting said 1-methylcyclopentanol with a suitable amount of an alkali metal hypochlorite in the presence of a carboxylic acid to form 1-methylcyclopentyl hypochlorite; and (e) heating said 1-methylcyclopentyl hypochlorite for a sufficient period of time to form 6-chloro-2-hexanone.

In conjunction with step (a) above, cyclohexanol (CH) is a commercially available starting material. The conversion of CH to cyclohexene (CHE) is accomplished by a dehydration step in which CH is heated in the presence of a suitable catalyst for a sufficient period of time to form CHE. The dehydration is conducted at a temperature of from about 150° C. to about 350° C., preferably from about 200° C. to about 250° C. The catalyst used is silica, which has been found to be exceptionally functional in this reaction. The time required to conduct this dehydration is from about one minute to about six hours or longer.

In conjunction with step (a) above, CHE is then subjected to a rearrangement step wherein CHE is converted to 1-methylcyclopentene (MCPE) by heating CHE in the presence of a suitable catalyst for a sufficient period of time to form MCPE. This rearrangement is generally conducted at a temperature higher than that temperature used in step (a) and is generally from about 250° C. to about 500° C., preferably from about 275 ° C. to about 450° C. The catalyst used in this rearrangement is also silica, for similar reasons stated above. The time required to conduct this rearrangement is from about one minute to about six hours.

In conjunction with step (c) above, MCPE is then subjected to a hydration step wherein MCPE is converted to 1-methylcyclopentanol (MCPO) by contacting said MCPE with a resin catalyst at a temperature lower than that used in step (b) in the presence of water and, preferably, in the presence of an organic solvent. This hydration step is generally conducted at a temperature of from about 20° C. to about 100° C., preferably from about 30° C. to about 90° C. Water can be supplied in any form as long as the desired end result is achieved, i.e. hydration. The organic solvent is any material which is suitable to facilitate the overall reaction. Such solvent can be miscible or immiscible with water, but preferably it is miscible. Suitable solvents include, without limitations, aliphatic, cycloaliphatic, aromatic hydrocarbons, ether, alcohols, and mixtures thereof. In many cases, cyclic ethers and/or aliphatic alcohols have particularly proven their worth. Solvents include polar liquids which can be used in accordance with the instant invention which include lower alkanols including cycloalkanols, e.g., those having from one to eight carbon atoms, such as methanol, ethanol, isopropanol (2-propanol), butanol, pentanol, cyclohexanol, and cyclobutanol, as well as polar asymmetrically halogenated hydrocarbons, e.g., those having from one to eight carbon atoms, such as chloroform, trifluorotrichloroethane, and trichlorofluoromethane, and mixtures thereof. Aliphatic alcohols having from one to six carbon atoms are desirable. In view of its good solubility in water, isopropanol is strongly recommended.

The resin catalyst used in this step (c) is generally an acidic ion exchange resin and preferably a strongly acidic cation exchange resin. Commercially available strongly acidic cation exchange can be used in the present invention. Among them, cation exchange resins of sulfonated styrene-divinylbenzene cross-linked polymer are preferred. There are two types of strongly acidic cation exhange resins; one is the porous type, made of porous resins, and the other one is the gel type which is made of nonporous resins. Suprisingly, the gel type can be used in the present invention as well as the porous-type. Sometimes, it is desirable to treat the strongly acidic cation exchange resin with an acid to sufficiently remove $Na^+$ and the like and increase the substituted amount of $H^+$ prior to use. The batch agitation method and the fixed-bed flowing method are applicable to the contact of MCPE with the strongly acidic cation exchange resin, with the latter being more preferable. The period of time required for the contact is usually in the range in terms of liquid hourly space velocity (LHSV) of 2–5 $hr^{-1}$ on the basis of the solution of the MCPE, in the case of the fixed-bed flowing method, even though there is no specific need that the range must be maintained.

Suitable resin catalysts, for example, are available from Rohm and Haas Company and sold under the names Amberlyst 15, and from Dow Chemical and sold under the name Dowex 50WX8-100. The overall time required to conduct this hydration in step (c) is from about one minute to about six hours or longer.

In conjunction with step (d) above, the MCPO is then reacted with an alkali metal hypochlorite (AMH), in the presence of a carboxylic acid, to form 1-methylcyclopentyl hypochlorite (MCPH). The AMH is either sodium hypochlorite, calcium hypochlorite, or mixtures thereof. The amount of AMH employed is from about 1:1 to about 5:1, preferably from about 1:1 to about 3:1 molar ratio or equivalents of AMH to one mole of MCPO.

The temperature of the reaction mixture in this step (d) is from about $-10°$ C. to about 30° C., preferably from about 0° C. to about 20° C.

The carboxylic acid employed in step (d) has the general formula $RCO_2H$ wherein R is an alkyl group, straight or branched, having from 1 to 8 carbon atoms, i.e. $C_1$–$C_8$. Carboxylic acids (CA) which have been found to be suitable, include without limitation, acetic acid, propionic acid, butyric acid, isobutyric acid, caproic acid, and mixtures thereof. The amount of carboxylic acid employed in step (d) is that which is sufficient to effect an ease with which the reaction takes place. In general, the molar ratio of MCPO/CA is about 10:1 to about 1:10.

The amount of carboxylic acid employed is at least that stoichiometric amount which is necessary to react with AMH to generate the reactive species "HOCl", and which has a significant effect on the yield of CHO and any impurities. In this regard, the molar ratio (or equivalents) of CA used is from about 1:1 to about 5:1, preferably from about 1:1 to about 2:1 of CA to one mole of MCPH. It is critical that such CA be used in step (d) since it has been found that the total absence thereof results in no formation of CHO.

In conjunction with step (e) above, the heating step (to convert the MCPH to CHO) is conducted at a temperature of at least 30° C., preferably from about 30° C. to about 60° C. The time required for this heating step is at least one minute, preferably from about one minute to about six hours.

As will be seen from the following examples, a combination of time, temperature concentrations, and acid (CA) provides a novel and efficient process which has heretofore not been obtainable.

The following specific examples are supplied for the purpose of better illustrating the invention. These examples are not intended, however, to limit or restrict the scope of the invention in any way and should not be construed as providing conditions, parameters, or values which must be utilized exclusively in order to practice the present invention. The time required to convert MCPO to MCPH is from about one minute to about six hours.

EXAMPLE 1

Dehydration of Cyclohexanol to form Cyclohexene—Step (a)

The equipment used was a glass (reactor) tube (0.78 inches diameter by 24 inches high) provided with an electric heater surrounding the tube. The tube was connected at the bottom thereof with a 250 ml glass flask positioned in an ice bath. The top of the tube was provided with two inlets. The first inlet was for the injection of nitrogen gas to blanket the system and the second inlet was provided with a tube to inject the starting materials into the system. The reactor tube was filled with 60 grams of 5 mm $SiO_2$ spheres. The feed (starting materials) was composed of 78.9 grams cyclohexanol dissolved in 8.8 grams of methanol. The feed was injected into the reactor tube at a rate of 1.03 cc/min and the nitrogen gas was used at a rate of 25 cc/min. The reactor tube was preheated to 250° C. and the feed injected into it at the above rate for a period of ninety minutes. The product, after the dehydration, was shown by GC to be cyclohexene. The cyclohexene collected was 63.1 grams with a conversion rate of 100% and a selectivity and yield of 97.5%.

EXAMPLE II

Rearrangement of Cyclohexene to form 1-Methylcyclopentene—Step (b)

Using similar equiment as that disclosed in Example I, the cyclohexene was fed to a silica-containing reactor tube at a rate of 0.99 cc/min along with nitrogen at 25 cc/min. The feeding rate lasted 75 minutes. The reactor tube was held at a temperature of 400° C. The overall yield was 59.1 grams with a conversion rate of 91.4%. The GC analysis showed that 1-methylcyclopentene (MCPE) was produced and that the yield was 60.3%.

EXAMPLE III

Hydration of 1-Methylcyclopentene (MCPE) to form 1-Methylcyclopentanol (MCPO)— Step (c)

The equipment used was a ⅜ inch diameter stainless steel tube (20 cc volume) with a 10 inch height. The tube was fitted with an oil heater jacket which maintained the reaction temperature at 80° C. The reactor tube was filled with 13 cc (7.7 grams) of dry Amberlyst 15 resin catalyst. The MCPE (4.1 grams—0.05 ml) was mixed with 18.0 grams (1.0 ml) water and 25.0 grams isopropanol (IPA) and the resultant mixture fed via a pump to the reactor tube at a rate of 0.46 cc/minute. The top of the reactor tube was fitted with a back pressure regulator and a flask to receive the product. The reactor was heated to 80° C. while a mixture of 1/1 IPA/$H_2O$ was pumped through the resin catalyst bed. After leveling out, the pump was switched to the MCPE feed. After the MCPE feed was pumped through the bed, the pump was again switched to the 1/1 IPA/$H_2O$ for 30 minutes. The product was collected only during the MCPE feed addition and the 30-minute flush. GC analysis showed that MCPO was produced with a 41.9% conversion of the MCPE. The MCPO yield was 22.9%.

EXAMPLE IV–XXXIX

The MCPO prepared according to Examples I–II above is then converted to CHO through steps (d) and (e) described above.

It has been reported in literature (U.S. Pat. No. 2,675,402) that 1-methylcyclopentyl hypochlorite rearranges to 6-chloro-2-hexanone. The best isolated yield reported for this rearrangement, in which NaOCl was generated in-situ by reacting $Cl_2$ with NaOH, was 72%. Replacing insitu generation of bleach with commercially available bleach gave 64% yield of 6-chloro-2-hexanone (isolated).

The reaction goes through an intermediate hypochlorite which rearranges to the chlorohexanone at low temperatures (30°–40° C.). It was important to understand the mechanistic details of each step of this reaction prior to setting up an experimental design. This was achieved through $^1$H NMR experiments. Using the results from the NMR experiments, a Plackett-Burman experimental design was developed to evaluate the reaction variables summarized below:

| VARIABLES | RANGES | | |
| --- | --- | --- | --- |
| | Low | Medium | High |
| Hypochlorite (mol. eq) | 1.5 | 2.25 | 3 |
| Acetonitrile (mol. eq) | 3.8 | 5.8 | 7.7 |
| Acetic Acid (mol. eq) | 1.7 | 3.5 | 5.2 |
| Stir rate (rpm) | 200 | 300 | 400 |
| Type of hypochlorite ion | | Ca or Na | |

The indicated low values were selected because they gave the 64% yield of 6-chloro- 2-hexanone mentioned above. Sodium hypochlorite, sold as a solution in water (5.25%), was used for that run. Calcium hypochlorite, unlike sodium hypochlorite, is sold as a crystalline solid, so higher concentrations of the reaction mixture can be maintained. The high values were selected to determine if the yields increased with the increases in the variables. Analysis of the products from early reactions showed a major impurity. Mass spectroscopy of the major impurity indicated a dichloro compound. It was decided to determine the influence of these variables on dichloro compound formation as well. Tables 1–7 set forth the results of these examples IV–XXXIX. The equivalency of these entries in Tables 1–7 to the examples IV–XXXIX is shown below:

| Table | Entry Nos. | Example Nos. |
| --- | --- | --- |
| 1 | 1–13 | IV–X |
| 2 | 1–4 | XI–XIX |
| 3 | 1–6 | XX–XXV |
| 4 | 1–3 | XXVI–XXVIII |
| 5 | 1–3 | XXVII–XXIX |
| 6 | 1–6 | XXX–XXXV |
| 7 | 1–4 | XXXVI–XXXIX |

In all of the Examples, bleach was maintained at 0° C. during the addition of 1-methylcyclopentanol at an addition rate of 3 ml/min and the reaction mixture stirred at room temperature for two hours. The subsequent rearrangement of the hypochlorite was conducted at 50° C. The results of the experimental design mentioned above are shown in Table 1. The responses that were evaluated were 6-chloro-2-hexanone yield, dichloro percent and conversion of 1-methylcyclopentanol. Statistical analysis was conducted using the SIMCA-P statistical package.

The strongest predictors for 6-chloro-2-hexanone yield were acetonitrile (increasing the amount of acetonitrile decreased the amount of 6-chloro-2-hexanone) and acetic acid (increasing the amount of acetic acid increased the amount of 6-chloro-2-hexanone). The strongest predictor for dichloro was acetic acid (increasing the amount of acetic acid increased the amount of the dichloro compound). Also, sodium hypochlorite gave better yields (besides being less expensive) than calcium hypochlorite.

Based on the statistical analysis, several additional experiments (Tables 2–7) were then conducted to further improve the conditions for the formation of 6-chloro-2-hexanone. The following conclusions were drawn from the experiments (based on GC yields):

Effect of acetonitrile (Table 2): Acetonitrile was initially used as a solvent to dissolve 1-methylcyclopentanol and acetic acid. Reducing the amount of acetonitrile to a minimum without decreasing the yield would decrease the price of 6-chloro-2-hexanone. Eliminating acetonitrile from the reaction gave an 88% GC yield of 6-chloro-2-hexanone which was comparable to the runs with acetonitrile (compare entry 4 with entries 1, 2, and 3 in Table 2).

Effect of acetic acid (Table 3): A stoichiometric amount of acetic acid is necessary for the rearrangement since it reacts with sodium hypochlorite to generate the reactive species "HOCl" and so it has a significant effect on the yield of 6-chloro-2-hexanone and the dichloro impurity. It was therefore important to adjust the amount of acetic acid such that it maximized the 6-chloro-2-hexanone formed and minimized the dichloro impurity. Using 1.5 equivalents of acetic acid gave 86% yield [entry 2 (GC yield) in Table 3] of 6-chloro-2-hexanone while decreasing the dichloro impurity from 4 wt % to 2 wt % [compare entry 1 to entry 2 (GC yield) in Table 3]. Decreasing the amount of acetic acid to 1.25 equivalents gave 81% yield [entry 3 (GC yield) in Table 3] of 6-chloro-2-hexanone while the amount of dichloro impurity was not detectable by GC under these conditions. Decreasing the amount of acetic acid further decreased the yield of 6-chloro-2-hexanone dramatically (entries 4 and 5 in Table 3). No 6-chloro-2-hexanone was detected in the absence of an acid (entry 6 in Table 3).

Effect of isobutyric acid (Table 4): Substituting isobutyric acid for acetic acid (partially or wholly) gave GC yields of 85–86% yield which was comparable to the 88% yield obtained by using acetic acid (compare entries 2 and 3 with entry 1 in Table 4).

Effect of Bleach (Table 5): Typically excess bleach was used to carry out the rearrangement. Further experiments were carried out to minimize the amount of bleach. The reaction works well [88% (GC yield)] with 1.25 molar equivalents of sodium hypochlorite. Lowering the amount of bleach (along with the acetic acid) also decreases the dichloro impurity in the reaction (compare entries 2 and 3 with entry 1 in Table 5).

Effect of temperature (Table 6): The dichloro impurity is presumed to be formed by the chlorination of 6-chloro-2-hexanone which means that during the formation of 1-methylcyclopentyl hypochlorite at room temperature, some of it rearranges to 6-chloro-2-hexanone which in turn may get chlorinated further to the dichloro impurity. At 0° C. the yield of 6-chloro- 2-hexanone essentially remained identical (86–89%-GC yields) to the 25 ° C. run. The dichloro impurity decreased and in some cases was not detectable by GC (compare entry 2 with 1, entry 4 with 3, and entry 6 with 5, all in Table 6).

Effect of other solvents for extraction (Table 7): Attempts were directed towards replacing methylene chloride with an environmentally friendlier solvent. The best alternative solvent (ethyl acetate) gave an 82% GC yield (entry 2 in Table 7).

The best yield of 6-chloro-2-hexanone, with the least amount of impurities (as detected by GC), was obtained using 1.25 molar equivalents of sodium hypochlorite and 1.25 molar equivalents of acetic acid (entry 4 in Table 6). 6-Chloro-2-hexanone was isolated by distilling it from the reaction mixture. The experiments were done under two different sets of conditions.

1) Using 1.5 molar equivalents of sodium hypochlorite 3.8 molar equivalents of acetonitrile and 1.7 equivalents of acetic acid gave 80% isolated yield of 6-chloro-2-hexanone.

2) Using 1.4 molar equivalents of sodium hypochlorite and 1.25 equivalents of acetic acid gave 80% isolated yield of 6-chloro-2-hexanone.

TABLE 1

| ENTRY | NaOCl (Bleach) MMOL EQ | Amt. of ACN ML; MOLAR EQ. | Amt. of AcOH ML; MOLAR EQ. | STIR RATE RPM | ION TYPE | GC YIELD* CHO YIELD % | DICHLORO WT % | OTHER IMPURITIES WT % | CONVERSION, % |
|---|---|---|---|---|---|---|---|---|---|
| 1 | 1.5 | 20;7.7 | 15;5.2 | 400 | Na | 90 | 13.5 | <0.6% | 99 |
| 2 | 3 | 10;3.8 | 15;5.2 | 400 | Na | 74 | 12.6 | 6.4 | 98 |
| 3 | 1.5 | 10;3.8 | 5;1.7 | 400 | Na | 92 | 1.6 | 1.2 | 99 |
| 4 | 3 | 20;7.7 | 15;5.2 | 200 | Na | 87 | 8 | 2.2 | 98 |
| 5 | 1.5 | 20;7.7 | 5;1.7 | 200 | Na | 86 | 2.2 | 1.2 | 98 |
| 6 | 3 | 10;3.8 | 5;1.7 | 200 | Na | 90 | 0.8 | 1.8 | 98 |
| 7 | 2.25 | 15;5.8 | 10;3.5 | 300 | Na | 82 | 13.6 | 0.6 | 99 |
| 8 | 3 | 20;7.7 | 5;1.7 | 400 | Ca | 80 | 2.4 | 5.6 | 96 |
| 9 | 1.5 | 10;3.8 | 5;1.7 | 200 | Ca | 86 | 0.8 | 0.8 | 93 |
| 10 | 1.5 | 20;7.7 | 15;5.2 | 200 | Ca | 86 | 4.8 | 3.2 | 95 |
| 11 | 3 | 10;3.8 | 15;5.2 | 200 | Ca | 91 | 8.8 | 3.2 | 98 |
| 12 | 1.5 | 10;3.8 | 15;5.2 | 400 | Ca | 93 | 13.8 | <0.6% | 100 |
| 13 | 2.25 | 15;5.8 | 10;3.5 | 300 | Ca | 87 | 4.6 | <0.6% | 98 |

All reactions were run using 5 g of 1-methylcyclopentanol. The mixture of 1-methylcyclopentanol, acetonitrile and acetic acid was added to bleach (3 ml/min) which was maintained at 0° C., the resultant reaction mixture was stirred at room temperature for 2 h, extracted with methylene chloride, washed with sodium bicarbonate and dried over $Na_2SO_4$. The subsequent rearrangement was carried out at 50° C.
*The yield of 6-chloro-2-hexanone was based on its response factor. The response factor of 6-chloro-2-hexanone was used to calculate the yields of impurities. The limit of detection is 0.6%.

TABLE 2

Effect or Acetonitrile

| ENTRY | NaOCl (Bleach) MMOL EQ | Amt of ACN ML; MOLAR EQ. | Amt. of AcOH ML; MOLAR EQ. | GC YIELD* CHO YIELD % | DICHLORO WT % | OTHER IMPURITIES WT % | CONVERSION, % |
|---|---|---|---|---|---|---|---|
| 1 | 1.5 | 20;7.7 | 15;5.2 | 90 | 13.5 | <0.6% | 99 |
| 2 | 1.5 | 10;3.8 | 5;1.7 | 92 | 1.6 | 1.2 | 99 |
| 3 | 3 | 20;7.7 | 15;5.2 | 87 | 6.4 | 2.2 | 98 |
| 4 | 1.5 | — | 5;1.7 | 88 | 4 | 1 | 100 |

All reactions were run using 5 g of 1-methylcyclopentanol. The mixture of 1-methylcyclopentanol and acetic acid was added to bleach (3 ml/min) which was maintained at 0° C. The stir rate was maintained at 400 rpm.. The resultant reaction mixture was stirred at room temperature for 2 h, extracted with methylene chloride, washed with sodium bicarbonate and dried over $Na_2SO_4$. The subsequent rearrangement was carried out at 50° C.
*The yield of 6-chloro-2-hexanone was based on its response factor. The response factor of 6-chloro-2-hexanone was used to calculate the yields of the impurities. The limit of detection is 0.6%.

TABLE 3

Effect of Acid

| ENTRY | Amt. of ACN ML; MOLAR EQ. | Amt. of AcOH ML; MOLAR EQ. | GC YIELD* CHO YIELD % | DICHLORO WT % | OTHER IMPURITIES WT % | CONVERSION % |
|---|---|---|---|---|---|---|
| 1 | — | 5;1.7 | 88 | 4 | 1 | 100 |
| 2 | — | 4.3;1.5 | 86 | 2.4 | <0.6% | 99 |
| 3 | — | 3.6;1.26 | 81 | <0.6% | 2 | 98 |
| 4 | — | 3.1;1.08 | 65 | <0.6% | 4 | 88 |
| 5 | — | 2.9;1.01 | 42 | <0.6% | 5 | 85 |
| 6 | 10;3.8 | 0;0 | <0.6% | <0.6% | <0.6% | 71 |

All reactions were run using 5 g of 1-methylcyclopentanol. The mixture of 1-methylcyclopentanol and acetic acid was added to bleach (3 ml/min) which was maintained at 0° C. The stir rate was maintained at 400 rpm.. The resultant reaction mixture was stirred at room temperature for 2 h, extracted with methylene chloride, washed with sodium bicarbonate and dried over $Na_2SO_4$. The subsequent rearrangement was carried out at 50° C.
*The yield of 6-chloro-2-hexanone was based on its response factor. The response factor of 6-chloro-2-hexanone was used to calculate the yields of the impurities. The limit of detection was 0.6%.

TABLE 4

Effect of Isobutyric acid

| ENTRY | Amt. of RCOOH ML; MOLAR EQ. | GC YIELD* CHO YIELD % | DICHLORO WT % | OTHER IMPURITIES WT % | CONVERSION % |
|---|---|---|---|---|---|
| 1 | 5;1.7 Acetic acid | 88 | 4 | 1 | 100 |
| 2 | 7;1.5 Isobutyric acid | 86 | 2.4 | 1.2 | 99 |
| 3 | 1.4;0.3 Isobutyric acid 4;1.4 Acetic acid | 85 | 5.6 | 2.8 | 100 |

All reactions were run using 5 g of 1-methylcyclopentanol. The mixture of 1-methylcyclopentanol and acetic acid and/or isobutyric acid was added to bleach (3 ml/min) which was maintained at 0° C. The stir rate was maintained at 400 rpm.. The resultant reaction mixture was stirred at room temperature for 2 h, extracted with methylene chloride, washed with sodium bicarbonate and dried over $Na_2SO_4$. The subsequent rearrangement was carried out at 50° C.
*The yield of 6-chloro-2-hexanone was based on its response factor. The response factor of 6-chloro-2-hexanone was used to calculate the yields of the impurities. The limit of detection was 0.6%.

TABLE 5
Effect of Bleach

| ENTRY | NaOCl (Bleach) MMOL EQ | Amt. of AcOH ML; MOLAR EQ. | GC YIELD* CHO YIELD % | DICHLORO WT % | OTHER IMPURITIES WT % | CONVERSION % |
|---|---|---|---|---|---|---|
| 1 | 1.5 | 5;1.7 | 88 | 4 | 1 | 100 |
| 2 | 1.4 | 3.6;1.25 | 89 | <0.6% | 1.4 | 99 |
| 3 | 1.25 | 3.6;1.25 | 88 | 2.3 | 1.3 | 99 |

All reactions were run using 5 g of 1-methylcyclopentanol. The mixture of 1-methylcyclopentanol and acetic acid was added to bleach (3 ml/min) which was maintained at 0° C. The stir rate was maintained at 400 rpm.. The resultant reaction mixture was stirred at room temperature for 2 h, extracted with methylene chloride, washed with sodium bicarbonate and dried over $Na_2SO_4$. The subsequent rearrangement was carried out at 50° C.
*The yield of 6-chloro-2-hexanone was based on its response factor. The response factor of 6-chloro-2-hexanone was used to calculate the yields of the impurities. The limit of detection was 0.6%.

TABLE 6
Effect of Temperature

| ENTRY | TEMPERATURE FOR HYPOCHLORITE FORMATION; °C. | NaOCl (Bleach) MMOL EQ | Amt. of RCOOH ML; MOLAR EQ. | GC YIELD* CHO YIELD % | DICHLORO WT % | OTHER IM- PURITIES WT % | CONVERSION % |
|---|---|---|---|---|---|---|---|
| 1 | rt | 1.4 | 3.6;1.25 Acetic acid | 89 | <0.6% | 1.4 | 99 |
| 2 | 0 | 1.4 | 3.6;1.25 Acetic acid | 89 | <0.6% | <0.6% | 100 |
| 3 | rt | 1.25 | 3.6;1.25 Acetic acid | 88 | 1.6 | 1 | 99 |
| 4 | 0 | 1.25 | 3.6;1.25 Acetic acid | 89 | <0.6% | <0.6% | 100 |
| 5 | rt | 1.5 | 7;1.5 Isobutyric acid | 86 | 2.4 | 1.2 | 99 |
| 6 | 0 | 1.5 | 7;1.5 Isobutyric acid | 89 | 0.8 | <0.6% | 100 |

All reactions were run using 5 g of 1-methylcyclopentanol. The mixture of 1-methylcyclopentanol and acetic acid and/or isobutyric acid was added to bleach (3 ml/min) which was maintained at 0° C. The stir rate was maintained at 400 rpm. The resultant reaction mixture was stirred at 0° C. or right for 2 h, extracted with methylene chloride, washed with sodium bicarbonate and dried over $Na_2SO_4$. The subsequent rearrangement was carried out at 50° C.
*The yield of 6-chloro-2-hexanone was based on its response factor. The response factor of 6-chloro-2-hexanone was used to calculate the yields of the impurities. The limit of detection was 0.6%.

TABLE 7
Effect of Other Extracting Solvents

| ENTRY | Amt. of RCOOH ML; MOLAR EQ. | EXTRACTING SOLVENT | GC YIELD* CHO YIELD % | DICHLORO WT % | OTHER IMPURITIES WT % | CONVERSION % |
|---|---|---|---|---|---|---|
| 1 | 5;1.7 acetic acid | methylene chloride | 88 | 4 | 1 | 100 |
| 2 | 7;1.5 isobutyric acid[1] | ethyl acetate | 82 | 2.8 | 0.8 | 99 |
| 3 | 5;1.5 acetic acid | methyl t-butyl ether | 71 | 4 | 4 | 98 |
| 4 | 5;1.5 acetic acid | methyl isobutyl ketone[2] | 81 | 2.4 | <0.6% | 85 |

[1]The acid used in this case was isobutyric acid but it's effect on the yield is very comparable to acetic acid.
[2]In this case the product was extracted with methyl isobutyl ketone, heated in the methyl isobutyl ketone solution at 50° C. and submitted for analysis.

TABLE 7-continued

Effect of Other Extracting Solvents

| ENTRY | Amt. of RCOOH ML; MOLAR EQ. | EXTRACTING SOLVENT | GC YIELD* CHO YIELD % | DICHLORO WT % | OTHER IMPURITIES WT % | CONVERSION % |
|---|---|---|---|---|---|---|

All reactions were run using 5 g of 1-methylcyclopentanol. The mixture of 1-methylcyclopentanol and the acid was added to 1.5 molar equivalents of bleach (3 ml/min) which was maintained at 0° C., the resultant reaction mixture was stirred at room temperature for 2 h, extracted with methylene chloride, washed with sodium bicarbonate and dried over $Na_2SO_4$. The subsequent rearrangement was carried out at 50° C.
*The yield of 6-chloro-2-hexanone was based on its response factor. The response factor of 6-chloro-2-hexanone was used to calculate the yields of the impurities. The limit of detection was 0.6%.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A process for preparing 6-chloro-2-hexanone which comprises the steps of (a) dehydrating cyclohexanol in the presence of a silica catalyst and at a temperature of at least about 150° C. and for a period of time in excess of about one minute to form cyclohexene; (b) rearranging said cyclohexene, at a higher temperature than in step (a), in the presence of a silica catalyst and for a period of time in excess of about one minute to form 1-methylcyclopentene; (c) hydrating said 1-methylcyclopentene, at a temperature lower than step (b) and in the presence of a resin catalyst for a period of time in excess of about one minute to form 1-methylcyclopentanol; (d) reacting said 1-methylcyclopentanol with an alkali metal hypochlorite in the presence of a carboxylic acid to form 1-methylcyclopentyl hypochlorite; and (e) heating said 1-methylcyclopentyl hypochlorite for a period of time in excess of about one minute to form 6-chloro-2-hexanone.

2. The process as set forth in claim 1 wherein the temperature in step (a) is from about 150° C. to about 350° C.

3. The process as set forth in claim 1 wherein the temperature in step (b) is from about 250° C. to about 500° C.

4. The process as set forth in claim 1 wherein the temperature in step (c) is from about 20° C. to about 100° C.

5. The process as set forth in claim 4 wherein there is also present an organic solvent.

6. The process as set forth in claim 1 wherein the carboxylic acid used in step (d) has the formula $RCO_2H$ where R is alkyl $C_1$–$C_8$.

7. The process as set forth in claim 6 wherein the carboxylic acid is isobutyric acid in step (d).

8. The process as set forth in claim 6 wherein the carboxylic acid is acetic acid in step (d).

9. The process as set forth in claim 1 wherein the temperature in step (a) is from about 200° C. to about 300° C.

10. The process as set forth in claim 1 wherein the temperature in step (d) is from about −10° C. to about 30° C.

11. The process as set forth in claim 1 wherein the temperature in step (e) is from about 30° C. to about 60°.

12. The process as set forth in claim 1 wherein the alkali metal hypochlorite, in step (d), is selected from the group consisting of sodium hypochlorite, calcium hypochlorite and mixtures thereof.

13. The process as set forth in claim 5 wherein the organic solvent is isopropanol in step (b).

14. The process as set forth in claim 1 wherein the carboxylic acid is a mixture of acetic acid and isobutyric acid in step (d).

15. A process for preparing 6-chloro-2-hexanone which comprises the steps of (a) dehydrating cyclohexanol in the presence of a silica catalyst and at a temperature of from about 150° C. to about 350° C. to form cyclohexene; (b) rearranging said cyclohexene at a temperature of from about 250° C. to about 500° C. in the presence of a silica catalyst to form 1-methylcyclopentene; (c) hydrating said 1-methylcyclopentene at a temperature of from about 20° C. to about 100 ° C. and in the presence of a resin catalyst to form 1-methylcyclopentanol; (d) reacting said 1-methylcyclopentanol with sodium hypochlorite in the presence of an acetic acid and at a temperature of from about 0 ° C. to about 20° C. to form 1-methylcyclopentyl hypochlorite; and (e) heating said 1-methylcyclopentyl hypochlorite at a temperature of from about 30° C. to about 60° C. to form 6-chloro-2-hexanone.

16. A process for preparing 6-chloro-2-hexanone which comprises the steps of (a) reacting 1-methylcyclopentanol with an alkali metal hypochlorite in the presence of a carboxylic acid to form 1-methylcyclopentyl hypochlorite; and (b) heating said 1-methylcyclopentyl hypochlorite to form 6-chloro-2-hexanone.

17. The process as set forth in claim 16, wherein the carboxylic acid used in step (a) has the formula $RCO_2H$ where R is alkyl $C_1$–$C_8$.

18. The process as set forth in claim 16 wherein the carboxylic acid is isobutyric acid in step (a).

19. The process as set forth in claim 16 wherein the carboxylic acid is acetic acid in step (a).

20. The process as set forth in claim 16 wherein the temperature in step (a) is from about −10° C. to about 50° C.

21. The process as set forth in claim 16 wherein the temperature in step (b) is from about 0° C. to about 20° C.

22. The process as set forth in claim 16 wherein the temperature in step (b) is from about 30° C. to about 60° C.

23. The process as set forth in claim 16 wherein the alkali metal hypochlorite is selected from the group consisting of sodium hypochlorite, calcium hypochlorite and mixtures thereof.

24. The process as set forth in claim 16 wherein the carboxylic acid is isobutyric acid in step (a).

25. The process as set forth in claim 16 wherein the carboxylic acid is a mixture of acetic acid and isobutyric acid in step (a).

26. A process for preparing 6-chloro-2-hexanone which comprises the steps of (a) reacting 1-methylcyclopentanol with sodium hypochlorite in the presence of acetic acid, and at a temperature of from about 0° C. to about 20° C. to form 1-methylcyclopentyl hypochlorite; and (b) heating at a temperature of from about 30° C. to about 60° C., said 1-methylcyclopentyl hypochlorite to form 6-chloro-2-hexanone.

27. A process for preparing 1-methylcyclopentanol which comprises the steps of (a) dehydrating cyclohexanol in the presence of a silica catalyst and at a temperature of at least about 150° C. and for a period of time in excess of about one minute to form cyclohexene; (b) rearranging said cyclohexene at a higher temperature than in step (a) in the presence of a silica catalyst to form 1-methylcyclopentene; (c) hydrating said 1-methylcyclo-pentene, at a temperature lower than step (b) and in the presence of a resin catalyst to form 1-methylcyclopentanol.

28. The process as set forth in claim 27 wherein the temperature in step (a) is from about 150° C. to about 350° C.

29. The process as set forth in claim 27 wherein the temperature in step (b) is from about 250° C. to about 500° C.

30. The process as set forth in claim 27 wherein the temperature in step (c) is from about 20° C. to about 100° C.

31. The process as set forth in claim 30 wherein there is also present an organic solvent.

* * * * *